United States Patent [19]

van der Burg et al.

[11] 4,039,558
[45] Aug. 2, 1977

[54] AMINO-SUBSTITUTED TETRACYCLIC COMPOUNDS

[75] Inventors: Willem Jacob van der Burg, Heesch; Robert Raymond Malvine Salsmans, Oss, both of Netherlands

[73] Assignee: Akzona Incorporated, Asheville, N.C.

[21] Appl. No.: 624,197

[22] Filed: Oct. 20, 1975

[30] Foreign Application Priority Data

Oct. 28, 1974 Netherlands ................... 7414038

[51] Int. Cl.² ............... C07D 487/02; C07D 498/02; C07D 513/02
[52] U.S. Cl. .................. 260/326.5 B; 260/239 D; 260/326.27; 260/326.28; 260/326.29; 260/326.31; 260/326.5 S; 260/326.5 A; 260/326.82; 260/326.84; 260/326.85
[58] Field of Search ............... 260/326.55, 326.5 B, 260/326.5 SA, 326.85, 326.82, 326.84

[56] References Cited

U.S. PATENT DOCUMENTS

| | | | |
|---|---|---|---|
| 3,636,045 | 1/1972 | Blattner et al. | 260/326.5 SA |
| 3,860,606 | 1/1975 | Van der Berg | 260/309.7 |
| 3,892,695 | 7/1975 | Van der Berg | 260/256.4 F |

*Primary Examiner*—Donald G. Daus
*Assistant Examiner*—Mary Vaughn
*Attorney, Agent, or Firm*—Francis W. Young; Hugo E. Weisberger

[57] ABSTRACT

The invention is dealing with compounds of the general formula:

as well as the pharmaceutically acceptable salts thereof, in which

X represents oxygen, sulphur, the group $>NR_7$ or the group $-CR_8R_9-$, $R_1$, $R_2$, $R_3$ and $R_4$ represent hydrogen, hydroxy, halogen, an alkyl, alkoxy or alkylthio group or a trifluoromethyl group, $R_5$ and $R_6$ represent hydrogen, an alkyl group or an aralkyl group, $R_7$ represents hydrogen or alkyl (1–4 C), $R_8$, $R_9$ represent hydrogen or methyl, and Q represents hydrogen (2H) or oxygen, having valuable antihistamine, sedative and antidepressive properties.

5 Claims, No Drawings

AMINO-SUBSTITUTED TETRACYCLIC COMPOUNDS

The present invention relates to novel biologically active tetracyclic compounds and to a process for the preparation of these novel compounds.

It was found that compounds of the general formula I:

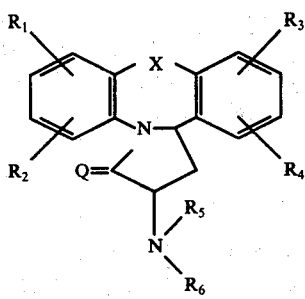

as well as the pharmaceutically acceptable salts thereof, in which
- X represents oxygen, sulphur, the group >$NR_7$ or the group —$CR_8R_9$—,
- $R_1$, $R_2$, $R_3$ and $R_4$ represent hydrogen, hydroxy, halogen, an alkyl, alkoxy or alkylthio group or a trifluoromethyl group,
- $R_5$ and $R_6$ represent hydrogen, an alkyl group or an aralkyl group,
- $R_7$ represents hydrogen or alkyl (1–4 C),
- $R_8$, $R_9$ represent hydrogen or methyl, and
- Q represents hydrogen (2H) or oxygen, possess valuable biological activities.

By "alkyl" in the definition of the substituents is preferably meant (unless otherwise indicated) a branched or unbranched alkyl group with 1–6 carbon atoms, such as methyl, ethyl, propyl, isopropyl, butyl, isobutyl, tert. butyl, n-pentyl, isopentyl or hexyl.

The alkyl group in the alkoxy or alkylthio moieties has a similar meaning.

An aralkyl group mentioned in the definition of $R_5$ and $R_6$ is preferably a phenylalkyl group, in which the alkyl group contains 1–4 carbon atoms, such as benzyl, phenylethyl, phenylpropyl, phenylisopropyl or phenylbutyl.

The compounds according to the invention may be prepared in a manner commonly used for analogous compounds.

For example the present compounds I can be prepared conveniently from a compound of general formula II:

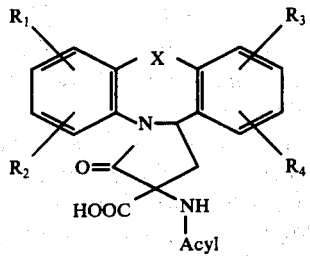

or an ester thereof,
in which $R_1$, $R_2$, $R_3$, $R_4$ and X have the meaning indicated above and acyl signifies an acyl group, preferably an aliphatic (1–6 C) or araliphatic (7–10 C) acyl group, such as formyl, acetyl, propionyl, butyryl, valeryl, caproyl, benzoyl, phenylacetyl, phenylprionyl, phenylbutyryl or cinnamoyl.

The compounds of formula I, in which Q is oxygen, may be prepared by a decarboxylation of a compound of general formula II under acidic or alcaline conditions. This decarboxylation is carried out in the usual manner, preferably at the boiling temperature of the reaction-mixture and results in a splitting off of the carboxyl group and in a simultaneous hydrolysis of the N-acyl moiety. The primary amines obtained in this manner may additionally be alkylated, aralkylated or acylated, using for example alkylhalides, aralkylhalides, acid halides or anhydrides respectively. For the introduction of N-methyl groups the method of Eschweiler-Clarke is preferred.

The compounds obtained in this manner are characterized by the general formula:

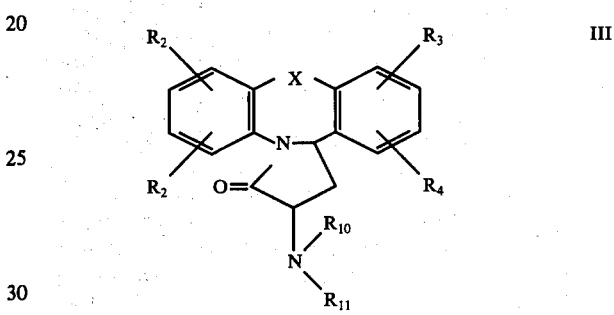

or a salt thereof, in which $R_1$, $R_2$, $R_3$, $R_4$ and X have the meanings above indicated and $R_{10}$ and $R_{11}$ have the same meanings as $R_5$ and $R_6$, but may further represent an aliphatic (1–6 C) or araliphatic (7–10 C) acyl group.

Decarboxylation of a compound of formula II under weak acidic, neutral or mild alcaline conditions results directly in a compound of formula III, in which $R_{10}$ or $R_{11}$ represent an acyl group and the other is hydrogen. Under these reaction conditions a hydrolysis of the N-acyl moiety does not take place.

The compounds of formula I, in which Q is hydrogen (2H) can be obtained by reduction of the carbonyl group of a compound of formula III. This reduction is carried out in the usual manner, preferably by means of diborane or a complex metalhydride, such as $LiALH_4$. The optionally present N-acyl group ($R_{10}$, $R_{11}$) is reduced simultaneously in this reduction, for example a N-formyl group is reduced to N-methyl, N-acetyl to N-ethyl, or N-phenylacetyl to N-phenylethyl.

The starting products II required in the above methods can be prepared in various manners. The attached flow sheet shows two methods for the preparation of compounds II, in which X is methylene. Other compounds II can be prepared in a similar manner.

The final product I contains two asymmetric centres, so that besides a mixture of two racemic diastereoisomers I, also the separate racemic diastereoisomers or the separate optically active diastereoisomers can be prepared. This mixture as well as the separate racemic or optically active diastereoisomers are numbered among the compounds of the invention.

The separate racemic or optically active diastereoisomers of formula I can be prepared from the mixture of the 2 diastereoisomers I by physical chemical techniques; such as counter current distribution, fractional crystallisation, column chromatography or preparative thin-layer chromatography, optionally followed by a resolution of the separate racemic diastereoisomer thus obtained in the usual manner, for example with the aid of an opticaly active acid, such as optically active tartaric acid.

The separate racemic or optically active diastereoisomers of formula I may further be prepared directly from the separate racemic or optionally active diastereoisomers of formula III. The latter method is even to be preferred Though the substituents $R_1, R_2, R_3$ and $R_4$ are preferably present already in the starting product II, it is also possible to introduce or to modify these substituents in the compounds of general formulae I or III, for example a hydroxyl group present can be converted to an alkoxy group, an amino group to hydroxy or halogen, a methoxy group to a hydroxy group, etc.

The unsubstituted or monosubstituted amines according to the general formula I ($R_5$ and/or $R_6 = H$) may, if desired, be alkylated in the usual manner, for example by reaction with an alkyl- or aralkylhalide. More usual for this purpose is, however, the acylation of the nitrogen atom in question, for example with an acid halide or anhydride, followed by the reduction of the keto group of the N-acyl derivative thus obtained. In regard to the introduction of methyl groups at the nitrogen atom, the procedure according to Eschweiler-Clarke (heating with a mixture of formaldehyde and formic acid) or the reaction with formaldehyde and sodiumcyanoborohydride in a suitable solvent, such as acetonitril, is to be preferred.

The pharmaceutically acceptable salts of the compounds according to the invention are acid addition salts and quaternary ammonium salts.

The novel compounds of formula I may be isolated from the reaction mixture in the form of an acid addition salt, depending on the conditions in which the reaction is carried out. The acid addition salts may also be obtained by treating the free base I with a pharmaceutically acceptable organic or inorganic acid. Suitable acids in this connection are: hydrochloric acid, hydrobromic- or hydroiodic acid, phosphoric acid, acetic acid, propionic acid, glycolic acid, fumaric acid, maleic acid, malonic acid, succinic acid, tartaric acid, citric acid, ascorbic acid, salicylic acid or benzoic acid.

The quaternary ammonium salts and in particular the lower (1–4 C) alkyl quaternary ammonium salts are obtained by reacting the compounds according to the general formula I with an alkyl halide, for example, methyliodide or methylbromide. The halogen anion may then further be replaced by other anions, such as a hydroxy anion, in the usual manner.

The compounds of the invention possess valuable biological activities. More in particular, the compounds I have marked antihistamine, sedative and antidepressive properties. They can be administered both enternally or parenterally, preferably in a daily dosage of from 0.01–10 mg/kg bodyweight.

Mixed with suitable excipients the compounds I can be compressed into solid dosage units such as pills, tablets, or coated tablets, or they can be processed into capsules.

With the aid of suitable liquids the compounds I may also be processed to solutions, emulsions or suspensions, intended for oral or parenteral administration.

Preferred compounds of the invention are the compounds of formula I, in which X represents methylene or oxygen, $R_1$, $R_2$, $R_3$ and $R_4$ represent hydrogen or a monosubstituent at one or both benzene rings selected from methyl, halogen or hydroxy and $R_5$ and $R_6$ represent hydrogen or a lower alkyl (1–4 C) group. More, in particular, the cis-stereoisomers of formula I are preferred in view of their superior biological activities.

In the examples the following nomenclature and numbering has been used:

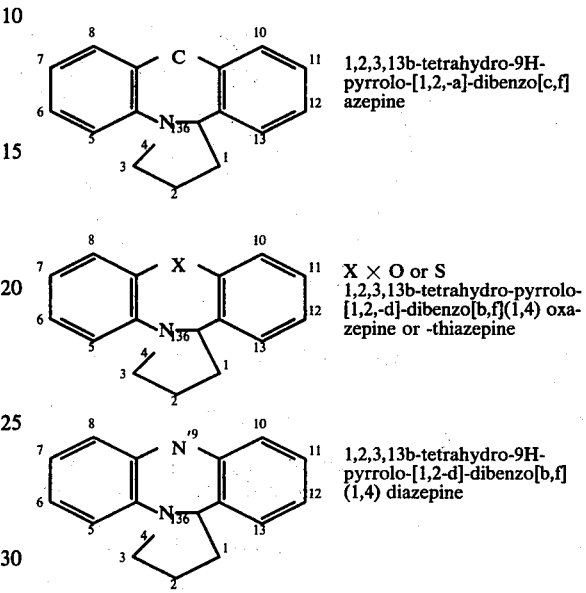

1,2,3,13b-tetrahydro-9H-pyrrolo-[1,2,-a]-dibenzo[c,f] azepine

X × O or S
1,2,3,13b-tetrahydro-pyrrolo-[1,2,-d]-dibenzo[b,f](1,4) oxazepine or -thiazepine 1,2,3,13b-tetrahydro-9H-pyrrolo-[1,2-d]-dibenzo[b,f] (1,4) diazepine

EXAMPLE 1

2-amino-3-oxo-1,2,3,13b-tetrahydro-9H-pyrrolo[1,2-a]-dibenzo[c,f] azepine

To 34,5 g of 2-acetylamino-2-ethoxycarbonyl-3-oxo-1,2,3,13b-tetrahydro-9H-pyrrolo[1,2-a]-dibenzo[c,f] azepine (oil, Rf in toluene: ethanol (9:2) = 0.5) are added 170 ml water and 10 ml concentrated $H_2SO_4$. The mixture is refluxed at 130° C for 18 hours, then cooled down and made alcaline with KOH. The mixture is extracted wtih methylenechloride and the extracts washed with water, dried and evaporated. Melting point 186°–188° C. Yield 97%.

EXAMPLE 2

2-dimethylamino-3-oxo-1,2,3,13b-tetrahydro-9H-pyrrolo]1,2-a]-dibenzo[c,f] azepine To 16,5 g of 2-amino-3-oxo-1,2,3,13b-tetrahydro-9H-pyrrolo-[1,2-]-dibenzo[c,f] azepine are added 20 ml of formic acid at 0° C. After adding 19 ml of formaldehyde (35%) the mixture is heated at 100° C for 20 hours. The mixture is then cooled down, after which 3,1 ml concentrated HCl is added and the volume of the reaction mixture concentrated by evaporation. Water is added to the oily residue after which the mixture is made alcaline with 40 ml NaOH (25%). The alcaline solution is extracted with methylenechloride. The extracts are washed with water, dried and washed evaporated. The oily residue obtained (18 g) is crystallised in ethanol/ether. Melting point (free base) is 120°–124° C. Melting point HCl salt: 285°–287° C.

EXAMPLE 3

2-dimethylamino-1,2,3,13b-tetrahydro-9H-pyrrolo[1,2-a]-dibenzo[c,f] azepine and salts To 1 gram of 2-dimethylamino-3-oxo-1,2,3,13b-tetrahydro-9H-pyrrolo[1,2-a]-dibenzo[c,f] azepine (melting point 120°-124° C), dissolved in 50 ml of diglyme, are added 1.14 ml of $BF_3$-etherate and 0.6 gram of sodiumborohydride.

The reaction mixture is heated to about 100° C and stirred at this temperature for 72 hours. The reaction mixture is then cooled down and concentrated by evaporation. To the oil obtained 40 ml of $HCl/H_2O$ (1:1) are added, after which the mixture is heated on a steam bath for 30 minutes. The mixture is cooled and made alcaline by adding a concentrated sodiumhydroxide solution. Extraction of this mixture with methylene-chloride followed by washing, drying and evaporation of the methylenechloride extracts yields 0.85 gram of the solid substance. Melting point 127°-130° C.

Treatment of this free base with an alcoholic fumaric acid solution yields the fumarate; melting point 219°-221° C. By recrystallisation of this fumarate from ethanol, the corresponding hemifumarate is obtained; melting point 230°-232° C.

Treatment of the free base with methyliodide yields the corresponding iodomethylate.

EXAMPLE 4

2-amino-12-methyl-3-oxo-1,2,3,13b-tetrahydro-pyrrolo[1,2-d]-dibenzo[b,f](1,4) oxazepine.HCl To 17,5 g of 2-acetylamino-2-methoxycarbonyl-12-methyl-3-oxo-1,2,3,13b-tetrahydro-pyrrolo[1,2-d]-dibenzo [b,f](1,4)-oxazepine are added 85 ml water and 5 ml conc. $H_2SO_4$. The mixture is refluxed for 19 hours and then cooled down and made alcaline with a concentrated NaOH solution. The mixture is extracted with ether, after which the ether extracts are washed with water, dried and evaporated. The oily residue is dissolved in ethylacetate. The solution is treated with an absorbent, then filtered and evaporated again. The oily residue is then treated with an alcoholic HCl solution yielding a crystalline product (14.3 g). Melting point HCl salt: 222°-224° C. The HCl salt obtained is identified as substantially the trans-isomer.

EXAMPLE 5

2-amino-12-methyl-3-oxo-1,2,3,13b-tetrahydro-pyrrolo[1,2-d]-dibenzo[b,f](1,4)-oxazepine.

The same compound as described in Example 4 is obtained directly from 3 gram 2-methyl-11-(2,2-diethoxy-carbonyl - acetylaminoethyl)-dibenzo[b,f](1,4)-oxazepine by refluxing this compound with 34 ml water and 2 ml concentrated $H_2SO_4$ for 20 hours, without isolating the intermediate compound 2-acetylamino-2-ethoxycarbonyl-12-methyl-3-oxo-1,2,3,13b-tetrahydro-pyrrolo-[1,2-d]-dibenzo [b,f](1,4)-oxazepine.

The compound is isolated from the reaction mixture by adding concentrated NaOH solution (to pH > 7) and extraction with ether.

The ether solution is evaporated. Melting point 104°-108° C (mixture of cis and trans compound). Yield 1.6 g (88%).

The mixture is dissolved again in ether and left stand for 24 hours at 5° C. The trans isomer crystallises and is filtered off. Melting point (trans isomer) 138°-142° C.

EXAMPLE 6

2-dimethylamino-12-methyl-3-oxo-1,2,3,13b-tetrahydro-pyrrolo[1,2-d]-dibenzo[b,f](1,4)-oxazepine.

30.9 g of the mixture of cis and trans compound, obtained in Example 5, is dissolved in 105 ml formic acid, to which is added 99 ml formaline (37%). The reaction mixture is heated at 100° C for 2.5 hours.

To this mixture is added 12.5 ml concentrated HCl solution, after which it is evaporated. The residue is dissolved in 500 ml water, made alcaline by the addition of 33% NaOH solution, and extracted with methylenechloride. The extracts are washed with water, dried and evaporated. Yield: 38 g oily residue. The residue is then dissolved in 100 ml alcohol/ether (1:1). To this solution are added 25 ml 30% alcoholic HCl solution. The trans-stereoisomer crystallises from this solution as the HCl salt (24.6 g). Melting point 242°-244° C. The mother liquor is chromatographed on $SiO_2$ using the solvent system toluene : ethanol (95:5). The cis-isomer is obtained as an oily substance (4.3 g). Melting point cis-isomer as oxalate: 215°-216° C.

EXAMPLE 7

2-dimethylamino-12-methyl-1,2,3,13b-tetrahydro-pyrrolo[1,2-d]-dibenzo[b,f](1,4)-oxazepine.

In the same manner as described in Example 3 the compounds obtained in Example 6 are reduced. Melting point trans-isomer (free base) : 134°-136° C. Melting point trans-isomer as HCl salt : 212°-215° C. Melting point cis-isomer (free base) : 119°-121° C.

EXAMPLE 8

2-amino-1,2,3,13b-tetrahydro-9H-pyrrolo[1,2-a]-dibenzo[c,f]azepine

To 0.4 gram of 2-amino-3-oxo-1,2,3,13b-tetrahydro-9H-pyrrolo-[1,2-a]-dibenzo[c,f]-azepine (melting point 186°-188° C), dissolved in 30 ml of diglyme, 0.5 ml of $BF_3$-etherate and 0.3 mg of $NaBH_4$ in nitrogen atmosphere are added. The reaction is carried out in a closed ampoule.

The ampoule is placed in an oil bath of 100° C. The reaction mixture is stirred magnetically at this temperature for 4 days. Then the mixture is cooled and evaporated. The residue is diluted with a mixture of 10 ml of concentrated HCl and 10 ml of water, after which the solution is heated on a steam bath for about 30 minutes. After cooling down a concentrated NaOH solution is added to the mixture (pH > 7). Extraction of this alcaline mixture with methylenechloride, followed by washing, drying and evaporation of the methylenechloride extracts yields 0.3 gram of the oily title product.

In the same manner as described before, the following compound is prepared: 2-amino-12-methyl-1,2,3,13b-tetrahydro-pyrrolo[1,2-d]-dibenzo[b,f](1,4)-oxazepine.

EXAMPLE 9

2-dimethylamino-12-methyl-1,2,3,13b-tetrahydro-pyrrolo[1,2-d]-dibenzo[b,f](1,4)-oxazepine 1 gram of 2-amino-12-methyl-1,2,3,13b-tetrahydro-pyrrolo[1,2-d]-dibenzo[b,f](1,4)-oxazepine (substantially trans-isomer) is dissolved in 3.7 ml of formic acid, after which while cooling 3.5 ml of formaline (37%) are added. The mixture is then stirred on a steam bath for 20 hours.

After cooling the mixture, 0.5 ml of concentrated HCl is added after which the mixture obtained is evaporated to dryness in vacuo as much as possible. The oily residue is diluted with 10 ml water and then made alcaline with a NaOH solution. The alcaline mixture is extracted with methylenechloride and the extracts washed, dried and evaporated to dryness. Yield: 1 gram of oil, from which the title product crystallises after some time. Melting point: 131°-134° C. This compound is identified as substantially the transisomer.

In the same manner is prepared:
2-dimethylamino-1,2,3,13b-tetrahydro-9H-pyrrolo[1,2-a]-dibenzo[c,f]-azepine-fumarate (substantially trans-isomer). Melting point 215°-220° C.

EXAMPLE 10

In the same manner as described in the examples 5, 6 and 7 are prepared:

2-dimethylamino-3-oxo-1,2,3,13b-tetrahydro-9H-pyrrolo[1,2-a]-dibenzo[c,f]-azepine (cis-isomer)
2-dimethylamino-1,2,3,13b-tetrahydro-9H-pyrrolo[1,2-a]-dibenzo[c,f]-azepine (cis isomer)
2-dimethylamio-3-oxo-1,2,3,13b-tetrahydro-pyrrolo[1,2-d]-dibenzo[b,f](1,4)-oxazepine (cis + trans)
2-dimethylamino-1,2,3,13b-tetrahydro-pyrrolo[1,2-d]-dibenzo[b,f](1,4)-oxazepine (cis + trans)
2-amino-3-oxo-6-trifluoromethyl-1,2,3,13b-tetrahydro-pyrrolo[1,2-d]-dibenzo[b,f](1,4)-oxazepine (cis + trans)
2-dimethylamino-3-oxo-6-trifluoromethyl-1,2,3,13b-tetrahydro-pyrrolo[1,2-d]-dibenzo[b,f](1,4)-oxazepine (cis-isomer and trans-isomer)
2-dimethylamino-6-trifluoromethyl-1,2,3,13b-tetrahydro-pyrrolo[1,2-d]-dibenzo[b,f](1,4)-oxazepine (cis-isomer and trans-isomer)
2-dimethylamino-12-chloro-1,2,3,13b-tetrahydro-pyrrolo[1,2-d]-dibenzo[b,f](1,4)-oxazepine (cis-isomer and trans-isomer)
2-dimethylamino-12-chloro-3-oxo-1,2,3,13b-tetrahydro-pyrrolo[1,2-d]dibenzo[b,f](1,4)-oxazepine (cis-isomer and trans-isomer)
2-amino-6-chloro-3-oxo-1,2,3,13b-tetrahydro-pyrrolo[1,2-d]-dibenzo[b,f](1,4)-thiazepine (cis + trans)
2-dimethylamino-6-chloro-3-oxo-1,2,3,13b-tetrahydro-pyrrolo[1,2-d]-dibenzo[b,f](1,4)-thiazepine (cis-isomer and trans-isomer)
2-dimethylamino-6-chloro-1,2,3,13b-tetrahydro-pyrrolo[1,2-d]-dibenzo[b,f](1,4)-thiazepine (cis-isomer and trans-isomer)
2-dimethylamino-12-methyl-3-oxo-1,2,3,13b-tetrahydro-9H-pyrrolo[1,2-a]-dibenzo[c,f]-azepine (cis-isomer and trans-isomer)
2-dimethylamino-12-methyl-1,2,3,13b-tetrahydro-9H-pyrrolo[1,2-a]-dibenzo[c,f]-azepine (cis-isomer and trans-isomer)
2-dimethylamino-1,2,3,13b-tetrahydro-pyrrolo[1,2-d]-dibenzo[b,f](1,4)-thiazepine (cis + trans)
2-dimethylamino-7-chloro-1,2,3,13b-tetrahydro-9H-pyrrolo[1,2-a]-dibenzo[c,f]-azepine (cis + trans)
2-dimethylamino-12-methoxy-1,2,3,13b-tetrahydro-9H-pyrrolo[1,2-a]-dibenzo[c,f]-azepine (cis + trans)
2-dimethylamino-6-methyl-1,2,3,13b-tetrahydro-pyrrolo[1,2-d]-dibenzo[b,f](1,4)-oxazepine (cis + trans)
2-dimethylamino-10-methyl-1,2,3,13b-tetrahydro-pyrrolo[1,2-d]-dibenzo[b,f](1,4)-oxazepine (cis + trans)
2-dimethylamino-9-methyl-1,2,3,13b-tetrahydro-9H-pyrrolo[1,2d]-dibenzo[b,f](1,4)-diazepine (cis + trans)
2-dimethylamino-9-methyl-12-trifluoromethyl-1,2,3,13b-tetrahydro-9H-pyrrolo[1,2-d]-dibenzo[b,f](1,4)-diazepine (cis + trans).

EXAMPLE 11

2-methylamino-1,2,3,13b-tetrahydro-9H-pyrrolo[1,2-a]-dibenzo[c,f]-azepine

To a suspension of 7.4 gram of LiAlH₄ in 100 ml of dry tetrahydrofuran a solution of 19 gram of 2-formylamino-3-oxo-1,2,3,13b-tetrahydro-9H-pyrrolo[1,2-a]dibenzo[c,f]-azepine (melting point 114° C) in 150 ml of dry THF is added under nitrogen atmosphere, while stirring.

The mixture is refluxed for one hour and then cooled down. Then 30 ml of water are carefully added and stirred for some minutes. The solid substance is filtered off and the filtrate is evaporated to dryness, yielding: 15.5 gram of the title product as an oily substance. Rf in methanol 0.2 on SiO₂.

Treating the product thus obtained with formaldehyde, followed by reduction with NaBH₄, yields 2-dimethylamino-1,2,3,13b-tetrahydro-9H-pyrrolo[1,2-a]-dibenzo[c,f]-azepine as a free base; melting point 124°-128° C.

EXAMPLE 12

In the manner described in Example 11 are prepared:

2-methylamino-12-methyl-1,2,3,13b-tetrahydro-9H-pyrrolo[1,2-a]-dibenzo[c,f]-azepine; by reduction of
2-formylamino-3-oxo-12-methyl-1,2,3,13b-tetrahydro-9H-pyrrolo[1,2-a]-dibenzo[c,f]-azepine
2-ethylamino-1,2,3,13b-tetrahydro-9H-pyrrolo[1,2-a]-dibenzo[c,f]-azepine, by reduction of
2-acetylamino-3-oxo-1,2,3,13b-tetrahydro-9H-pyrrolo[1,2-a]dibenzo[c,f]-azepine,
2-phenylethylamino-1,2,3,13b-tetrahydro-9H-pyrrolo[1,2-a]-dibenzo[c,f]-azepine, by reduction of
2-phenylacetylamino-3-oxo-1,2,3,13b-tetrahydro-9H-pyrrolo[1,2-a]-dibenzo[c,f]-azepine,
2-ethylamino-12-methyl-1,2,3,13b-tetrahydro-pyrrolo[1,2-d]-dibenzo[b,f](1,4)-oxazepine, by reduction of
2-acetylamino-3-oxo-12-methyl-1,2,3,13b-tetrahydro-pyrrolo[1,2-d]-dibenzo[b,f](1,4)-oxazepine.

FLOW-SHEET
Scheme I
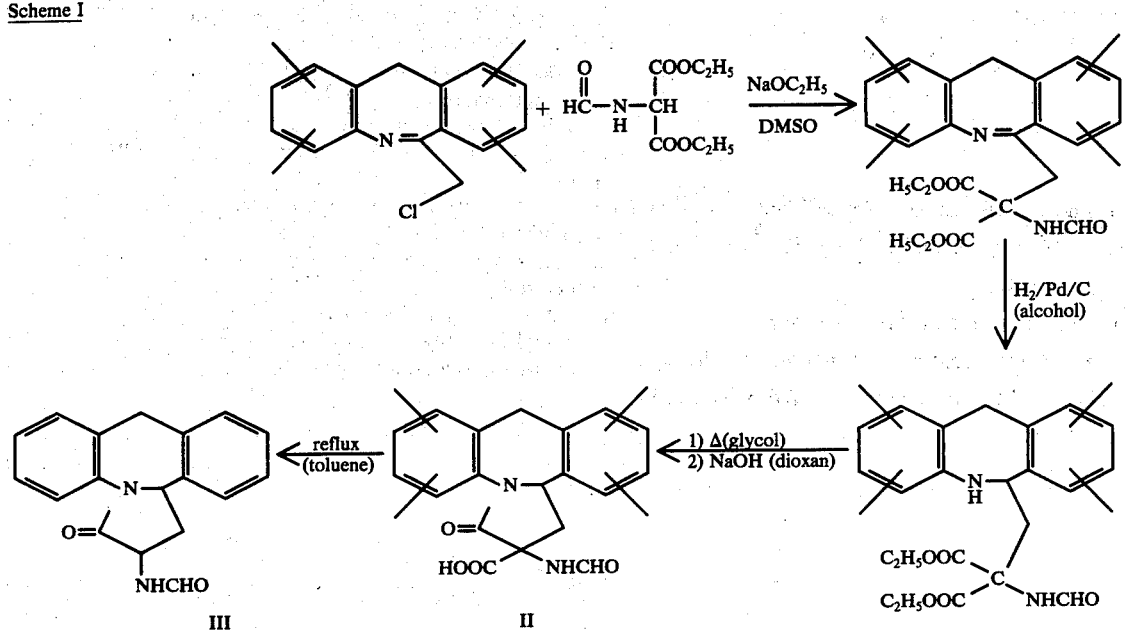
Scheme II
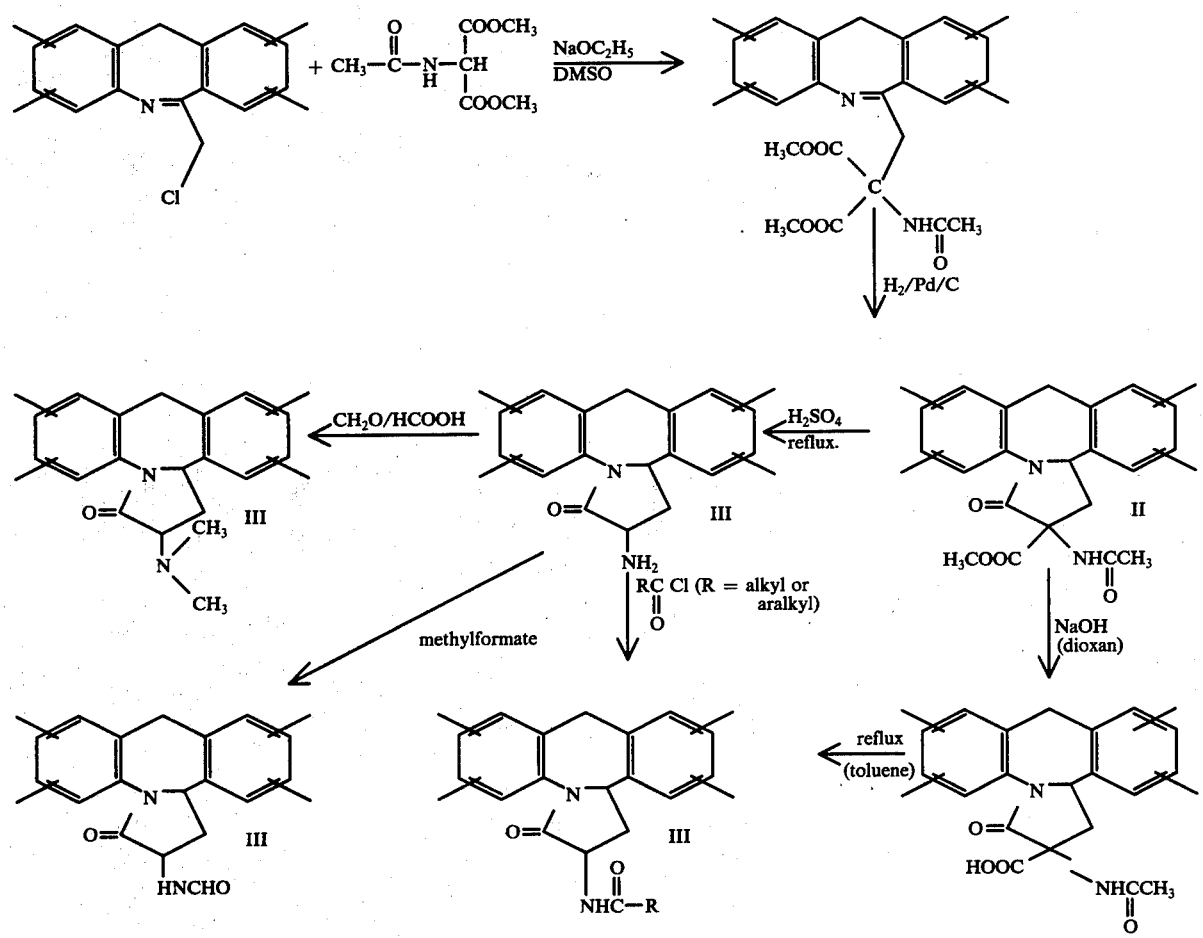
We claim:
1. A compound of the formula:

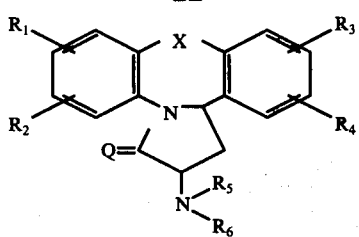

or a pharmaceutically acceptable salt thereof, in which

X represents oxygen, sulfur, the group $>NR_7$ or the group $-CR_8R_9-$,

Q represents hydrogen (2H) or oxygen, $R_1$, $R_2$, $R_3$, $R_4$ represent hydrogen, hydroxy, halogen, alkyl having 1 to 6 carbon atoms, alkoxy having 1 to 6 carbon atoms, alkylthio having 1 to 6 carbon atoms or trifluoromethyl, $R_5$, $R_6$ represent hydrogen, alkyl having 1 to 6 carbon atoms or phenylalkyl the alkyl group of which has 1 to 4 carbon atoms, $R_7$ represents hydrogen or alkyl having 1 to 4 carbon atoms and $R_8$, $R_9$ represent hydrogen or methyl.

2. A compound according to claim 1, in which X is methylene.

3. A compound according to claim 1, in which X is oxygen.

4. The cis-stereo-isomer of a compound according to claim 1.

5. 2-Dimethylamino-1,2,3,13b-tetrahydro-pyrrolo[1,2-d]-dibenzo[b,f](1,4)-oxazepine and the pharmaceutically acceptable salts thereof.

* * * * *